US00PP25892P3

(12) United States Plant Patent
Stoppel

(10) Patent No.: US PP25,892 P3
(45) Date of Patent: Sep. 15, 2015

(54) CHERRY ROOTSTOCK PLANT NAMED 'STO2'

(50) Latin Name: ***Prunus cerasus* L.×*P.*×*schmittii* Rehder**
Varietal Denomination: STO2

(71) Applicant: Peter Stoppel Obstbau, Kressbronn (DE)

(72) Inventor: Peter Stoppel, Kressbronn (DE)

( * ) Notice: Subject to any disclaimer, the term of this patent is extended or adjusted under 35 U.S.C. 154(b) by 91 days.

(21) Appl. No.: 13/987,742

(22) Filed: Aug. 27, 2013

(65) Prior Publication Data

US 2015/0067933 P1 Mar. 5, 2015

(51) Int. Cl.
*A01H 5/06* (2006.01)

(52) U.S. Cl.
USPC ..... Plt./183

(58) Field of Classification Search
USPC ..... Plt./183
See application file for complete search history.

(56) References Cited

PUBLICATIONS

UPOV hit on 'STO2', www3.wipo.int/pluto/user/en/index.jsp, application publication date Apr. 15, 2012, applicant Peter Stoppel.*
Canadian Plant Breeders' Rights Application, Apr. 24, 2015.
Plant Breeders' Rights Application filed in Turkey on Mar. 23, 2015.
Plant Breeders' Rights Application filed in Europe on Dec. 29, 2011.

* cited by examiner

*Primary Examiner* — Anne Grunberg
(74) *Attorney, Agent, or Firm* — Myers Bigel Sibley & Sajovec, PA

(57) ABSTRACT

A new and distinct cultivar of *Prunus* plant named 'STO2,' characterized by its weeping plant habit and typical slow growth; good adaptation at hot and dry conditions; and as a rootstock, slow vegetative growth that imparts uniformity, higher yield and better fertility to the grafted variety as compared to a standard rootstock such as Gisela 5, F12/1 and Mazzard.

3 Drawing Sheets

Latin name of the genus and species: The Latin name of the genus and species of the plant variety disclosed herein is *Prunus cerasus* L.×*P.*×*schmittii* Rehder.

Variety denomination: The inventive cultivar of *Prunus cerasus* L.×*P.*×*schmittii* Rehder disclosed herein has been given the varietal denomination 'STO2.'

BACKGROUND OF THE INVENTION

The present invention relates to a new and distinct cultivar of *Prunus* plant, typically used as a cherry tree rootstock, botanically known as *Prunus cerasus* L.×*P.*×*schmittii* Rehder, and hereinafter referred to by the name 'STO2.'

The new and distinct variety of cherry hybrid tree of the present invention was bred as a cross of *Prunus cerasus* with a *Prunus canescens* hybrid (*Prunus avium* and *Prunus canescens*) in Germany in 1989. It has been successfully asexually propagated by tissue culture. The purpose of breeding program was to find a better adapted cherry rootstock. The new *Prunus* plant is better adapted on heat and aridity than other rootstocks with a slow vegetative growth. The breeder also succeeded in creating a new cherry rootstock, which has a higher yield and influences the grafted variety positively in fertility.

SUMMARY OF THE INVENTION

Plants of the new *Prunus* have not been observed under all possible environmental conditions. The phenotype may vary slightly with variations in environment such as temperature and light intensity without any variance in genotype.

The following traits have been repeatedly observed and are determined to be the unique characteristics of 'STO2.' These characteristics in combination distinguish 'STO2,' as a new and distinct cultivar of *Prunus:*

1. Weeping plant habit;
2. Good adaptation to hot and dry clime conditions;
3. As a rootstock, with slow vegetative growth, it produces a dwarf tree;
4. As a rootstock, imparts uniformity and higher yield to the grafted variety as compared to, for example, Gisela 5, F12/1 and Mazzard;
5. As a rootstock, trees are around 70% slower than on *Prunus avium* seedlings; that is, the trees, for which 'STO2' is used as rootstock, grow more slowly and thus result in a dwarf tree that is smaller than, for example, a *Prunus avium* seedling; and
6. Absence of suckers.

As used herein, "higher yield" refers to the impact of the rootstock of the tree on both vegetative as well as generative growth. Thus, the rootstock can affect the generative growth and assist the grafted species to achieve greater yield. Therefore, with regard to 'STO2,' the yield per tree and crown volume is higher than that of a standard rootstock such as Gisela 5, F12/1 and Mazzard.

Further with 'STO2' as the rootstock, the grafted variety can achieve better fertility (i.e., greater generative growth). That is, use of 'STO2' as a rootstock results in greater generative growth than in the case of standard rootstock (Gisela 5, F12/1, Mazzard); the tree produces more flowers, more fruit, with a greater yield of the same or larger fruit size. In the end greater output is achieved.

The parents of 'STO2' are partly a hybrid between *Prunus avium* and *Prunus canescens* (unnamed and not patented) and the other part a *Prunus cerasus* wild species (unnamed and not patented). The parent (*Prunus avium*×*Prunus canescens*) is known for stronger growth than the new hybrid (STO2). The parent (*Prunus avium*×*Prunus canescens*) grows perpendicularly, while the new cultivar ('STO2') grows pendulously. Further, the parent *Prunus cerasus* is known for a distinctly more rounded leaf than the new hybrid (STO2). Leaf of STO2: narrow and elongated, Leaf of parent *Prunus cerasus*: round.

Plants of the new *Prunus*, 'STO2', also can be compared to plants of *Prunus* 'GI 2091' (U.S. Plant Pat. No. 16,173, issued Dec. 27, 2005). In side-by-side comparisons conducted in Kressbronn, Germany, plants of the new *Prunus* differed primarily from plants of 'GI 2091' in the following characteristics:

1. As a rootstock, plants of the new *Prunus* have about 10% stronger growth (i.e., faster growth) in comparison to plants with 'GI 2091' rootstocks;
2. Plants of the new *Prunus* do not develop stipules, whereas 'GI 2091' plants develops stipules;
3. Plants of the new *Prunus* have a weeping habit, whereas 'GI 2091' plants have an upright habit; and
4. Due to its typical/characteristic growth, plants of the new *Prunus* impart higher yield to the scion plant than plants of 'GI 2091.'

'STO2' was first asexually propagated in autumn of 2001 in Freising, Germany, using tissue culture. Asexual reproduction of *Prunus* rootstock plant 'STO2' by tissue culture since autumn 2001 has shown that the unique features of this new variety are stable and the plant reproduces true to type in succeeding generations of asexual reproduction.

BRIEF DESCRIPTION OF THE DRAWINGS

The accompanying photographs illustrate the overall appearance of the new *Prunus* plant. These photographs show the colors as true as it is reasonably possible to obtain in colored reproductions of this type. Colors in the photographs may differ slightly from the color values cited in the detailed botanical description which accurately describe the colors of the new *Prunus* plant.

DETAILED BOTANICAL DESCRIPTION

Figure 1:
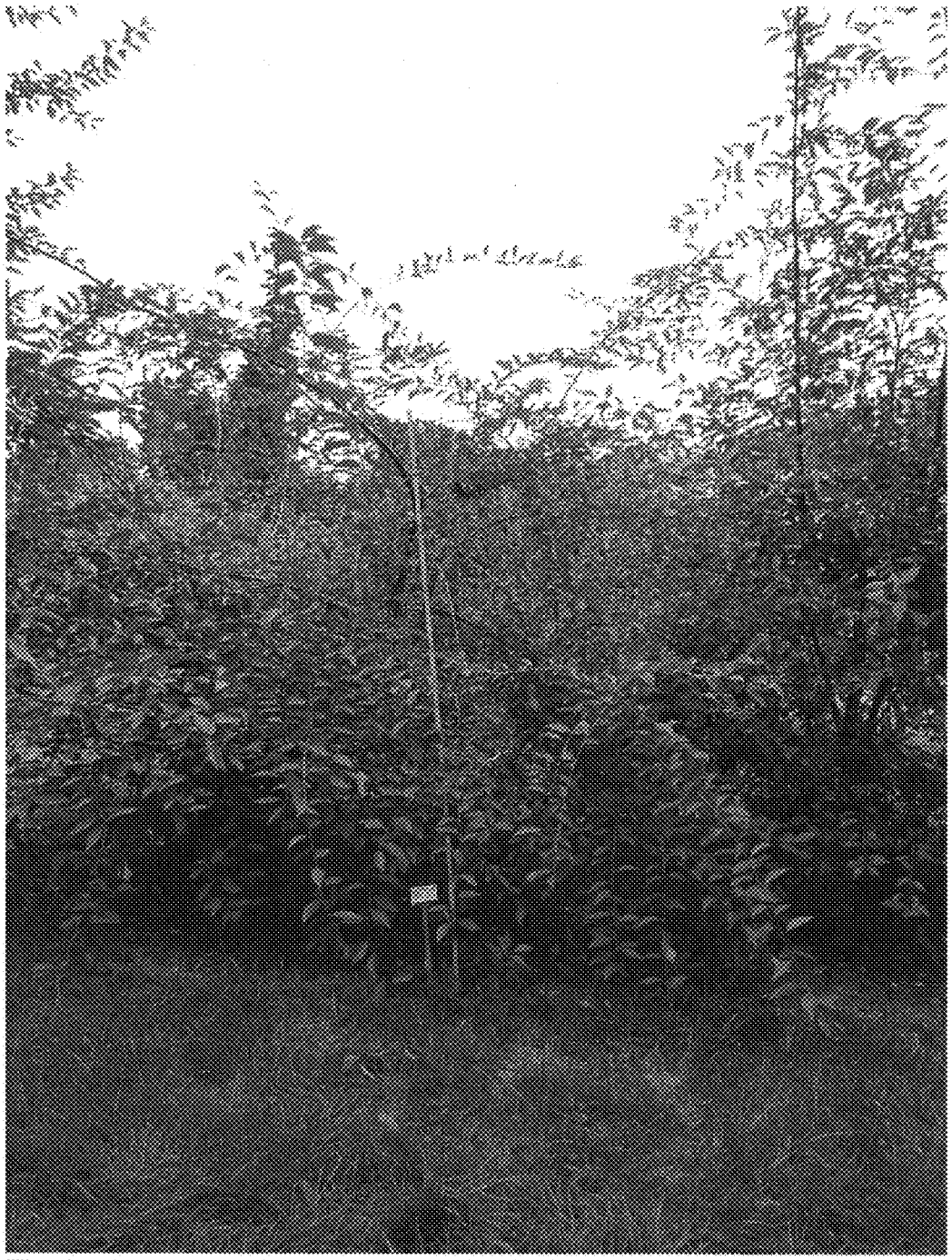
FIG. 1 provides a side perspective view of a typical tree of 'STO2' grown in an outdoor orchard.
Figure 2:
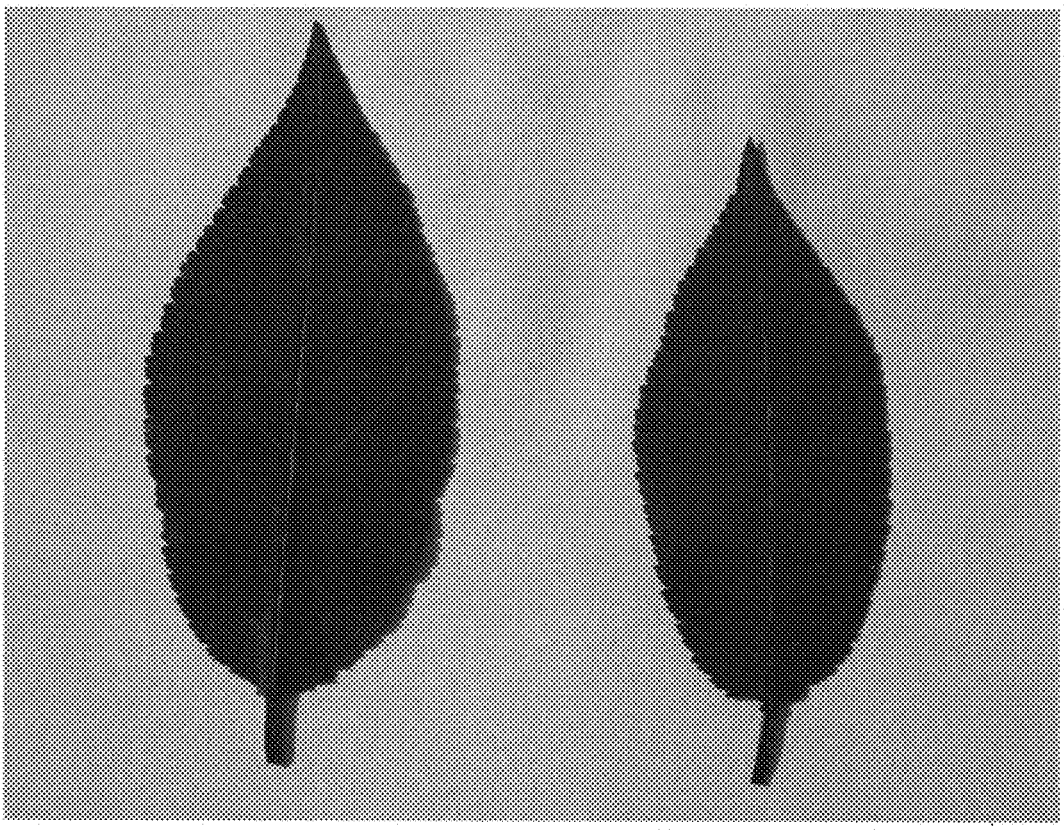
FIG. 2 provides a close-up view of leaves of a tree of 'STO2.'
Figure 3:
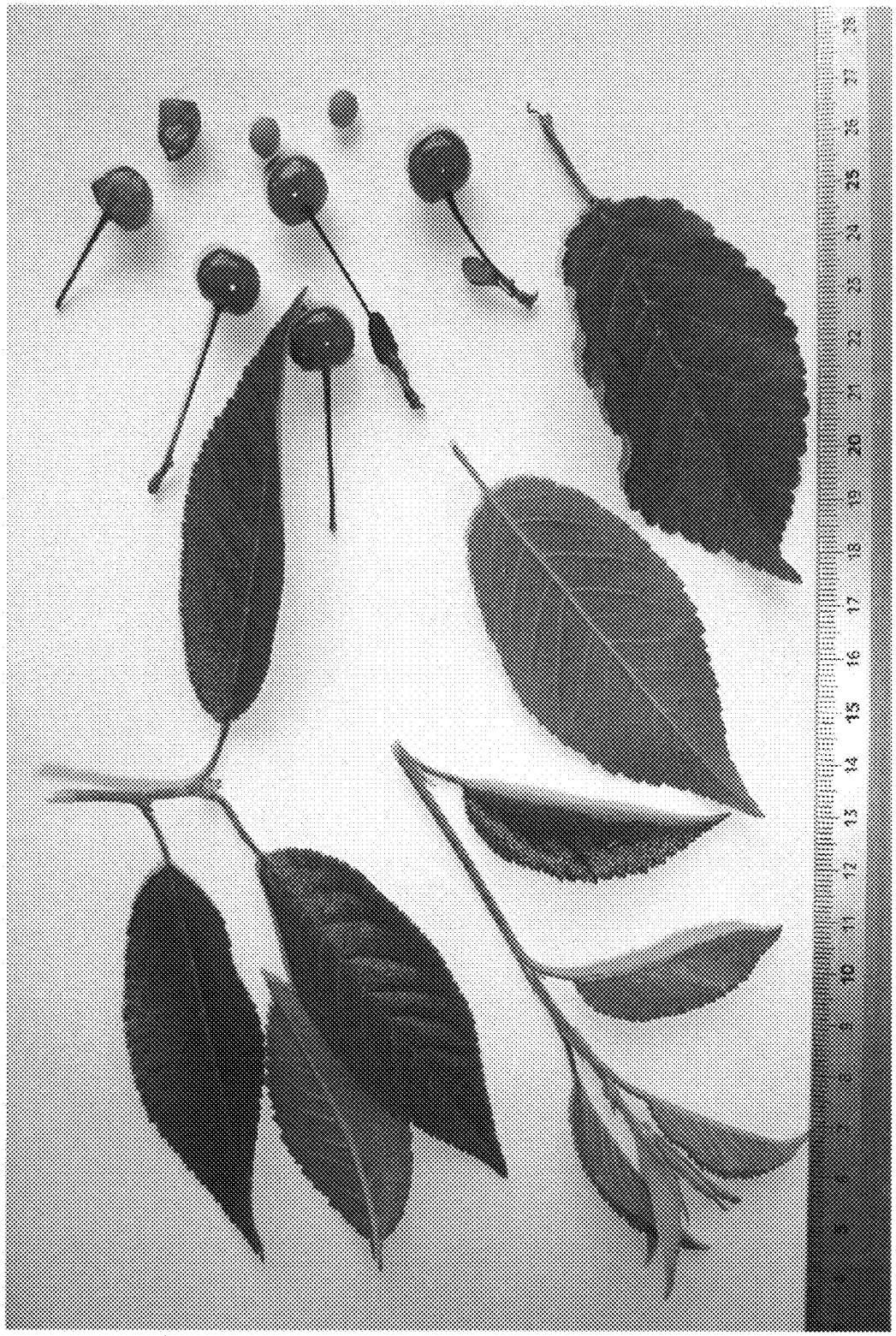
FIG. 3 provides a close-up view of fruits, branches and leaves of 'STO2.'

The aforementioned photographs, following observations and measurements describe plants grown during the summer in Kessbronn, Germany in an outdoor orchard and under conditions and practices generally used in commercial cherry production. Plants were 12 years old when the photographs and descriptions were taken. Measurements and numerical values represent averages for typical plants and plant parts. The actual measurements of any individual plant or plant parts, or any group of plants or plant parts, of the new *Prunus* plant may vary from the stated average. In the following description, color references are made to The Royal Horticultural Society (R.H.S.) Colour Chart, except where general terms of ordinary dictionary significance are used.

'STO2' has a generally arched plant habit and is slow in growth. The weeping plant habit is typical for the new *Prunus* plant. After twelve growing seasons in Kressbronn, Germany, a height of about 3.7 meters, a width of about 2.95 meters and a trunk diameter of about 9.3 cm were observed for 'STO2.' The growth reduction induced by 'STO2' allows a highly intensive cherry production with dwarf trees.

Botanical classification: *Prunus cerasus* L.×*P.*×*schmittii* Rehder 'STO2.'

Parentage: Breeding between *Prunus cerasus* and a *Prunus canescens* hybrid.

Propagation:

*Type*.—By asexual reproduction.

*Method*.—By tissue culture since the autumn of 2001 in a controlled environment. The process is similar to the propagation of other cherry rootstock.

Plant description:

*Plant use*.—Only as a rootstock.

*Plant form*.—Semi-ellipsoid form, after 3 years reflexed branching.

*Plant and growth habit*.—Weeping plant habit; plant are typically grown as a single stem; weak vigor (i.e., slow growth).

*Stem description*.—Strength: Strong. Texture: Rough. Color: Grey brownish RHS 199B.

*Leaf description, fully developed leaves*.—Arrangement: Alternate; simple. Length: About 8 cm to about 9.5 cm. Width: About 3.7 cm to about 4.5 cm. Shape: ovate, very elongated. Apex: Acute. Tip: Acuminate. Base: Obtuse, convex. Margin: Biserrate. Texture, upper surface: Glabrous. Texture, lower surface: Coarse, pubescent. Color: Fully developed leaves, Upper surface: Close to RHS 141B; Venation: Close to RHS 146C. Fully developed leaves, Lower surface: Close to 144A; Venation, Close to RHS 144C.

*Petiole description*.—Length: About 1.3 cm to about 1.9 cm. Diameter: About 0.2 cm. Color, upper surfaces and lower surfaces: Close to RHS161A.

*Presence of stipules*.—Absent.

Flower description:

*Flower type/habit*.—3 to 6 flowers single flowers arranged one compound panicles. Flowers occur in general on one year old branches.

*Fragrance*.—Weak, pleasant.

*Natural flowering season*.—In April, in south Germany, flowering occurs at about the same time as 'GI 2091,' patented cherry rootstock (U.S. Plant Pat. No. 16,173).

*Lastingness of entire bloom period*.—About 15 days.

*Lastingness of an individual bloom*.—About 8 days.

*Inflorescence height*.—About 3.5 cm to about 4 cm.

*Inflorescence diameter*.—About 2.5 cm to about 3.5 cm.

*Flower diameter*.—About 1.4 cm to about 1.8 cm.

*Flower depth*.—About 0.8 cm to about 1.1 cm.

*Bud length*.—4-8 mm.

*Bud width* (*bud diameter*).—2-3 mm.

*Bud shape*.—Cylindrical, acutely pointed at the projecting ends.

*Bud colour*.—Brown to light brown-RHS-165A.

*Bloom quantity*.—Fertile, a large quantity of flowers occur each year. Remarkably, the flowers occur on only the one year old branches.

*Petals*.—Arrangement: Five petals in a single whorl. Slightly overlapping. Length: About 0.5 cm to about 0.9 cm. Width: About 0.5 cm to about 0.7 cm. Shape:

Oblong, slightly elongated. Apex: Rounded, slightly elongated. Base: Truncate. Margin: Entire. Texture, upper and lower surfaces: Smooth, glabrous. Color: When fully opened, upper surface: Close to RHS 155B. When opening and fully opened, lower surface: Close to RHS 155B.

*Sepals*.—Arrangement: Five sepals in a single whorl. Length: About 0.3 cm. Width: About 0.11 cm to about 0.23 cm. Shape: Angular set, triangular, slightly elongated. Apex: Pointed. Base: Truncate. Margin: Entire. Texture, upper and lower surfaces: Smooth, glabrous. Color, upper surfaces: Close to RHS 142B. Color, lower surfaces: Close to RHS 145B.

*Pedicels*.—Length: About 1.5 cm to about 1.9 cm. Diameter: About 0.1 cm. Angle: About semi-erect to semi-prostrate from the inflorescence stalk. Texture: Smooth, glabrous. Color: Close to RHS 142A.

*Peduncle*.—Length: About 0.2 cm to about 1.1 cm. Diameter: About 0.2 cm. Surface: Smooth. Color: Close to RHS 149A.

*Reproductive organs*.—Stamens: Quantity per flower: Numerous. Filament length: About 4 mm to about 7 mm. Filament color: Close to RHS 155B. Anther length: About 0.3 mm to about 0.8 mm. Anther color: Close to RHS 6A. Pistils: Quantity per flower: One. Pistil length: About 8 mm to about 13 mm. Style length: About 6 mm to about 11 mm. Style color: Close to RHS 150C. Stigma shape: Round. Stigma color: Close to RHS 150A.

*Fruit description*.—Maturity when described. Date picking: July in south Germany, varies with climatic conditions. About the same time as 'GI 2091,' patented cherry rootstock (U.S. Plant Pat. No. 16,173). Size: very small to small about 1 cm to about 1.3 cm diameter. Average weight: 1.2 g, varies slightly with fertility of the soil, amount of thinning and climatic conditions. Form: Globose, Slightly flat at the apex. Stem cavity: Slightly obcordate to flat. Color: RHS 185A.

*Peduncle description*.—Size: Average length about 3.4 cm. Average diameter about 0.09 cm. Color: RHS 149A.

*Stone description*.—Average length: About 0.74 cm. Average width: About 0.6 cm. Average thickness: 0.55 cm. Form: Nearly globose. Base: round. Apex: Rounded. Color: RHS 163C when dry.

*Fruit use*.—Not to be used as a dessert fruit.

Pollination requirements: 'STO2' is not self-fertile and requires a pollinator.

Temperature tolerance: Plants of the new *Prunus* have been observed to tolerate temperatures from about −20° C. to about 40° C. Notably, under hot and dry climate climatic conditions, 'STO2' trees do not exhibit chlorosis. These trees are very robust in the presence of substantial variations in temperature (very low temperatures in winter (−20° C.) and very hot temperatures in summer (+40° C.)) and such temperature fluctuations have no negative effect on the trees.

Drought tolerance: Due to a deep root system, the 'STO2' variety is tolerant to drought conditions.

What is claimed is:

1. A new and distinct cultivar of *Prunus cerasus* L.×*P.*× *schmittii* Rehder plant named 'STO2,' substantially as illustrated and described herein.

* * * * *

UNITED STATES PATENT AND TRADEMARK OFFICE

CERTIFICATE OF CORRECTION

PATENT NO. : PP25,892 P3
APPLICATION NO. : 13/987742
DATED : September 15, 2015
INVENTOR(S) : Stoppel It is certified that error appears in the above-identified patent and that said Letters Patent is hereby corrected as shown below:

On Title Page:

(50) Latin Name: Please correct "*Prunus cerasus* L.xP.x*schmittii* Rehder"
to read -- *Prunus cerasus L.* x *P.* x *schmitti* Rehder --

In the Specification

Column 1, Line 3: Please correct "*Prunus cerasus* L.xP.x*schmittii* Rehder."
to read -- *Prunus cerasus L.* x *P.* x *schmitti* Rehder. --

Line 5: Please correct "*Prunus cerasus* L.xP.x*schmittii* Rehder"
to read -- *Prunus cerasus L.* x *P.* x *schmitti* Rehder --

Lines 12-13: Please correct "*Prunus cerasus* L.xP.x*schmittii* Rehder,"
to read -- *Prunus cerasus L.* x *P.* x *schmitti* Rehder, --

Column 2, Line 12, 5.: Please correct: "trees are around 70% slower than"
to read -- trees have around 70% slower growth than --

Column 3, Line 4: Please correct "(*Prunus aviumxPrunus canescens*)"
to read -- (*Prunus avium* x *Prunus canescens*) --

Line 6: Please correct "(*Prunus aviumxPrunus canescens*)"
to read -- (*Prunus avium* x *Prunus canescens*) --

Column 4, Lines 8-9: Please correct "*Prunus cerasus* L.xP.x*schmittii* Rehder"
to read -- *Prunus cerasus L.* x *P.* x *schmitti* Rehder --

Line 22: Please correct "Weeping plant habit; plant are"
to read -- Weeping plant habit; plants are --

Signed and Sealed this
Seventeenth Day of May, 2016

Michelle K. Lee

Michelle K. Lee
*Director of the United States Patent and Trademark Office*

In the Claims:

Column 6, Claim 1, Lines 29-30: Please correct "*Prunus cerasus* L.xP.x*schmittii* Rehder"
to read -- *Prunus cerasus L.* x *P.* x *schmitti* Rehder --